(12) United States Patent
Kumazawa et al.

(10) Patent No.: US 6,749,873 B2
(45) Date of Patent: Jun. 15, 2004

(54) CHEESE YIELD ENHANCING METHOD

(75) Inventors: Yoshiyuki Kumazawa, Kawasaki (JP); Jiro Sakamoto, Kawasaki (JP); Chiya Kuraishi, Kawasaki (JP); Noriki Nio, Kawasaki (JP); Shoji Sakaguchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/923,358

(22) Filed: Aug. 8, 2001

(65) Prior Publication Data
US 2002/0043159 A1 Apr. 18, 2002

(30) Foreign Application Priority Data
Aug. 31, 2000 (JP) ........................................ 2000-263616

(51) Int. Cl.$^7$ ................................................. A23C 9/12
(52) U.S. Cl. ............................. 426/36; 426/34; 426/38; 426/40; 426/42; 426/43; 426/582
(58) Field of Search ............................. 426/34, 36, 38, 426/40, 41, 42, 43, 580, 582

(56) References Cited

U.S. PATENT DOCUMENTS

| | | | |
|---|---|---|---|
| 4,205,090 A | | 5/1980 | Maubois et al. |
| 6,120,809 A | * | 9/2000 | Rhodes .......................... 426/36 |
| 6,224,914 B1 | * | 5/2001 | Han et al. ...................... 426/36 |

FOREIGN PATENT DOCUMENTS

| | | |
|---|---|---|
| DE | 247 832 A1 | 7/1987 |
| EP | 0 711 501 A1 | 5/1996 |
| EP | 0 711 504 A1 | 5/1996 |
| EP | 1 048 219 A2 | 11/2000 |
| JP | 57-501810 | 10/1982 |
| JP | 58-149645 | 9/1983 |
| JP | 64-27471 | 1/1989 |
| JP | 1-300889 | 12/1989 |
| JP | 2-131537 | 5/1990 |
| JP | 2-308756 | 12/1990 |
| JP | 4-126039 | 4/1992 |
| JP | 5-199883 | 8/1993 |
| JP | 6-225775 | 8/1994 |
| WO | WO 91/13553 | 9/1991 |
| WO | 91/13553 | 9/1991 |
| WO | 94/21129 | 9/1994 |
| WO | 94/21130 | 9/1994 |

OTHER PUBLICATIONS

Monti et al, Enzymatic solubilization of heat–denatured cheese whey protein, Journal of Dairy Science, 1978, 61(9), pp. 1233–1237.*
C.A. Barth, et al., *Nahrung*, vol. 41, No. 1, S., pp. 2–12, 1997(with English abstract).
E.F. Babiker, et al., *J. Agric Food Chem.*, vol. 44, pp. 3746–3750, 1996.
G.W. Jameson, et al., *Bulletin of the International Dairy Federation*, No. 313, pp. 3–8, 1996.
A–M Bech, *Int. Dairy Journal*, vol.3, pp. 329–342, 1993.
PJ. De Koning, et al, *Neth. Milk Dairy J.*, vol. 35, pp. 35–46, 1981.
A.A. Hofi, et al., *Egyptian J. Diary So.*, vol. 1, pp. 159–162, 1973.
N. Seki, et al., *Nippon Suisan Gakkaishi*, vol. 56(1), pp. 125–132, 1990 (with English abstract).

* cited by examiner

*Primary Examiner*—Leslie Wong
(74) *Attorney, Agent, or Firm*—Oblon, Spivak, McClelland, Maier & Neustadt, P.C.

(57) ABSTRACT

Herein is disclosed a cheese yield enhancing method in a cheese manufacturing method including a process of separating a cheese curd from a whey after a milk coagulating treatment of a material milk by a milk coagulating enzyme, said cheese yield enhancing method comprising steps of: adding/mixing a protein decomposing enzyme treated material of a milk whey protein (a partial hydrolysate of the milk whey protein) to the material milk; and subjecting a resulting mixture to the milk coagulating treatment by the milk coagulating enzyme, or said cheese yield enhancing method comprising steps of: adding/mixing a partial hydrolysate of a milk whey protein to the material milk; allowing transglutaminase to act on a resulting mixture; and subjecting the mixture to the milk coagulating treatment by the milk coagulating enzyme, whereby a yield of a cheese curd from a material milk, and therefore a yield of cheese may be enhanced and a cheese superior in quality may be manufactured.

22 Claims, 2 Drawing Sheets a) SKIM MILK b) SKIM MILK + WHEY PROTEIN DECOMPOSED MATERIAL c) SKIM MILK + WHEY PROTEIN DECOMPOSED MATERIAL + TG (REACTION: 0 MINUTE)

d) SKIM MILK + WHEY PROTEIN DECOMPOSED MATERIAL + TG (REACTION: 19.5 HOURS)

a) SKIM MILK + WHEY PROTEIN DECOMPOSED MATERIAL (●)

b) SKIM MILK + WHEY PROTEIN DECOMPOSED MATERIAL + TG (▲)

CHEESE YIELD ENHANCING METHOD

BACKGROUND OF THE INVENTION

1. Technical Field of the Invention

The present invention relates to a cheese manufacturing method, particularly to a cheese manufacturing method in which a cheese yield is enhanced by elaborately utilizing a milk whey protein (hereinafter referred to simply as a whey protein), or the whey protein and transglutaminase (hereinafter abbreviated as TG)

2. Prior Art

It is considered that a cheese originated when human beings began to raise livestock, that is, around 6,000 B.C. Generally, the cheese is roughly classified into a processed cheese and a natural cheese. The natural cheese is classified into ripen cheeses such as a super-hard cheese, hard cheese, semi-hard cheese, and soft cheese, and fresh cheeses subjected to no ripening process.

The cheese is manufactured according to a very exquisite and sophisticated principle. First, manufacturing of the ripen natural cheese will be described.

Examples of a milk as a raw material (material milk) include milks of a cow, goat, sheep, buffalo, reindeer, donkey, camel, and the like, and these are used not only in a whole milk but also in a semi-skim milk, skim milk, and the like. As well known, a milk coagulating enzyme called chymosin (or rennet) is added to the material milk, or a so-called cheese starter, and the like are used, if necessary or as desired, in the material milk to form a coagulated material (cheese curd) (milk coagulating treatment). A major protein in the material milk is casein, and is formed of $\alpha s1$-, $\alpha s2$-, $\beta$- and $\kappa$-casein. The casein forms a micelle structure and exists in the material milk. The $\kappa$-casein is distributed in the surface of a casein micelle, and contributes to stabilization of the micelle. Chymosin is an enzyme which cuts $\kappa$-casein by a specific site, and through the cutting, peptide (called glycomacropeptide (GMP)) on a C terminal end which is exposed on the surface of the casein micelle and which is highly hydrophilic is separated from $\kappa$-casein. GMP exists as a part of the whey protein after separated. After the cutting, remaining $\kappa$-casein is called para-$\kappa$-casein, and is highly hydrophobic peptide. Therefore, after chymosin acts on $\kappa$-casein, the highly hydrophobic para-$\kappa$-casein is distributed in the surface of the casein micelle, and the casein micelle becomes unstable. As a result, the casein coalesces, and forms a so-called cheese curd.

Subsequently, the cheese curd is finely cut, and a whey protein is separated (primary whey). Subsequently, the separated cheese curd is cleaned with a warm water, excessive lactose is removed and additionally the remaining whey protein is removed (secondary whey). Subsequently, the cheese curd is collected, and squeezed. After the curd is squeezed for a given time, salt is added to the curd. The curd is subjected to a ripening process, ripened for a given period, and formed into the natural cheese.

Additionally, as described above, the whey protein separated after the cheese curd is formed is a byproduct in the cheese manufacturing. The whey protein is mainly constituted of $\beta$-lactoglobulin, $\alpha$-lactoalbumin, serum albumin, IgG and GMP. At present, a part of the whey protein is used for manufacturing various foods and for feeding animals. A high nutritive value of the whey protein has been known long (Barth and Behnke; Nahrung, vol. 41, pp. 2 to 21, 1997), and effective use of the whey is considered to be also industrially very advantageous.

Moreover, as described above, in the cheese manufacturing, casein in a solid content of the material milk excluding whey components (lactose, whey protein, and the like) is a main cheese constituting component, and all solid contents of the material milk do not form the cheese. Therefore, in the industrial manufacturing of the cheese, it goes without saying that it is desirable from viewpoints of costs and effective utilization of a milk resource to be able to manufacture as much cheese as possible from a constant amount of the material milk. Moreover, there is another advantage that a product can be supplied to a consumer inexpensively by establishing a high-yield cheese manufacturing method. However, for a conventional cheese manufacturing technique, under existing circumstances, it cannot necessarily be said that a yield of the cheese curd is high. Enhancement of the yield of the cheese curd means that a casein fraction coagulated through chymosin treatment is quantitatively increased. That is, it is a technical problem to incorporate much whey protein in the cheese curd during preparation of the cheese curd.

Attempts have been made to reduce the whey protein discharged into the whey as much as possible and enhance the yield of the cheese curd. For example, a method of concentrating a volume of the material milk to about $\frac{1}{3}$ by ultrafiltration and using the material milk to manufacture the cheese is described in U.S. Pat. No. 4,205,090. PCT National Publication No. 501810/1982 describes a method of selectively concentrating the material milk by ultrafiltration to enhance an ion strength in the material milk, fermenting the material milk, removing water from the material milk, and using this raw material to manufacture the cheese. Furthermore, it is described in Japanese Patent Application Laid-Open No. 308756/1990 that when the whey secondarily produced during manufacturing of the cheese is concentrated, and the concentrated whey protein and concentrated material milk are used to manufacture the cheese, the obtained cheese curd contains a high concentration of the whey protein, and the whey protein as a resulting byproduct can effectively be utilized.

However, in these techniques, the material milk or the reused whey needs to be preprocessed by the ultrafiltration, and it is difficult to say that this is an industrially convenient method. Moreover, for the cheese manufacturing method in which the material milk treated by the ultrafiltration is used, it is known that with a short-term ripened cheese, a product quality is not affected. However, with a long-term ripened cheese, protein decomposition or cheese flavor generation is sometimes inhibited. This may supposedly be explained from facts that in the cheese rich in an unmodified whey protein the whey protein itself is not easily decomposed and the whey protein inhibits decomposition of casein by protease (Jameson and Lelierve; Bulletin of the IDF, vol. 313, pp. 3 to 8, 1996, deKoning et al.; Neth. Milk Dairy Journal, vol. 35, pp. 35 to 46, 1981, Bech; International Dairy Journal, vol. 3, pp. 329 to 342, 1993). In conclusion, it cannot be said that the existing cheese manufacturing technique by concentration of the material milk sufficiently satisfies the consumer in quality implications such as a flavor and texture.

In order to enhance the yield of the cheese curd, it is a technical problem to effectively incorporate the whey protein discharged in the whey into the coagulated casein by rennet treatment (coagulating treatment), that is, into the cheese curd, which has been described above. As one example of solution means of this problem, transglutaminase (TG) as a protein crosslinking enzyme is utilized. As well known, TG is an enzyme which catalyzes acyl transition reaction between γ-carboxyamide group of a remaining glutamine group in the protein and various first-class amines. When the first-class amine is an ε-amino group of lysine, an ε-(γ-glutamil)lysine crosslink is formed among a protein or polypeptide chain, and this crosslink can form a protein crosslinked polymer.

These days, TG has been used for manufacturing many foods such as a marine product made with a boiled fish paste, and a processed livestock product. Moreover, an example in which TG is also used in a dairy product has been reported. For example, in Japanese Patent Application Laid-Open No. 27471/1989, a cheese manufacturing method including a process of adding TG in a manufacturing process is described. However, in the described cheese manufacturing method, the cheese is manufactured from the curd formed using gluconodeltalactone and TG, or only TG without using rennet. This is different from the aforementioned cheese basic manufacturing principle. Moreover, in Japanese Patent Application Laid-Open No. 131537/1990, a method of using TG to manufacture a cheese food is described, but the cheese food as an object herein is manufactured by heating/melting the natural cheese or the processed cheese as the raw material. This is far different from the viewpoint of the cheese curd yield enhancement targeted by the present invention. In publication WO94-21129, a method of adding TG to the milk to manufacture a gel for an acid food is described. However, in this method, no rennet is added, and an object of the method is to manufacture a dairy product having an innovative texture without using emulsifier or stabilizer. Therefore, the viewpoint of the yield enhancement according to the present invention is not described in the publication.

Of course, the cheese manufacturing method using TG and rennet is described in the publication WO94-21130. However, different from a usual cheese manufacturing method, separation of the cheese curd from the whey is not described, and this method is far different from the cheese manufacturing method including the whey separation as the object of the present invention. Moreover, the yield enhancement is not described. Furthermore, in a publication EP0711504, a technique of treating a material milk with TG, heating and deactivating TG, adding rennet, and manufacturing the cheese is described. It is also described that the yield of the cheese curd can be enhanced. However, this cheese manufacturing method starts from the material milk itself. This is different from a method of adding/mixing a whey protein treated by a protein decomposing enzyme to the material milk, and subjecting this mixture directly to a milk coagulating treatment, or allowing TG to act on the mixture and subsequently subjecting the mixture to the milk coagulating treatment according to the present invention.

Additionally, as described above, some ideas that the whey protein is utilized to enhance the cheese yield have been reported. Moreover, some techniques of utilizing TG to manufacture the dairy product have also been reported. As described later, the present invention is based on an idea that the whey protein is incorporated into the cheese curd by transforming the whey protein to a partial hydrolysate, or by using the whey protein transformed into the partial hydrolysate together with TG.

Additionally, it is inherently known that the whey protein itself cannot easily undergo action of TG. This is supposedly because β-lactoglobulin, α-lactoalbumin, and serum albumin as the main components of the whey protein are all globular proteins having many disulfide bonds in molecules. The disulfide bond is a covalent bond, and is a remarkably stable bond. That is, the whey protein can be said to be a very stable globular protein which does not easily cause a structure change. In other words, as a cause why the whey protein does not easily undergo the TG action, a residual glutamine group or a residual lysine group necessary for undergoing the action is not distributed in the surface of the whey protein, and the protein cannot participate in crosslinking reaction. Alternatively, there is supposedly a situation in which a firm globular structure prevents the protein from easily contacting the enzyme. In fact, except the whey protein, for example, for actin as a muscle structure protein which is another globular protein, it is also remarkably difficult to undergo the TG action. From these facts, it cannot but be said that it is remarkably difficult to utilize TG and incorporate the whey protein into the cheese curd.

Additionally, an attempt to treat the protein with protease and allow TG to act on the protein has already been reported (Babiker et al.; Journal of Agricultural and Food Chemistry, vol. 44, pp. 3746 to 3750, 1996). It is also described that gluten as a wheat protein is treated with protease, TG is allowed to act on the protein, and gluten functional properties such as an emulsifiable property and bubbling property can be enhanced. Moreover, in Japanese Patent Application Laid-Open No. 126039/1992, a technique is described in which a bitter taste generated by the protease treatment can be reduced by TG treatment. However, these techniques are far different from the present invention whose object is to enhance the action of TG to the whey protein, also enhance the yield of the cheese curd, and finally enhance the cheese yield.

Additionally, a publication WO91-13553 discloses a technique of adding protease directly to the material milk, adding a material obtained by specifically hydrolyzing only the whey protein to another material milk, and using this material to manufacture the cheese. As described above, it is known that addition of an excessive whey protein inhibits generation of a flavor of the ripened cheese in the manufacturing of the natural cheese. An object of the technique disclosed in the WO91-13553 is to prevent this. This is far different in object and embodiment from the present invention in that there is no viewpoint of the yield enhancement and protease is added directly to the material milk in a mixed state of the whey protein and casein.

SUMMARY OF THE INVENTION

[Problem to be Solved by the Invention]

Under background of the aforementioned prior art, an object of the present invention is to provide a method for enhancing a yield of a cheese curd from a material milk and a yield of a cheese, and manufacturing a cheese superior also in quality.

[Means to Solve the Problems]

The present inventor has intensively studied enhancement of a yield of a cheese curd in cheese manufacturing in order to effectively utilize a milk resource. As a result, it has been found that an incorporated amount of a whey protein into the cheese curd is increased by elaborately using the whey protein during manufacturing of a cheese, or by elaborately using the whey protein and TG, and this achieves curd yield enhancement. The present invention has been completed based on such finding.

Accordingly, the present invention relates to a cheese yield enhancing method in a cheese manufacturing method including a process of separating a cheese curd from a whey after a milk coagulating treatment of a material milk by a milk coagulating enzyme, said cheese yield enhancing method comprising steps of: adding/mixing a protein decomposing enzyme treated material of a milk whey protein (a partial hydrolysate of the milk whey protein) to the material milk; and subjecting a resulting mixture to the milk coagulating treatment by the milk coagulating enzyme, and also to a cheese yield enhancing method in a cheese manufacturing method including a process of separating a cheese curd from a whey after a milk coagulating treatment of a material milk by a milk coagulating enzyme, said cheese yield enhancing method comprising steps of: adding/mixing a partial hydrolysate of a milk whey protein to the material milk; allowing transglutaminase to act on a resulting mixture; and subjecting the mixture to the milk coagulating treatment by the milk coagulating enzyme.

DETAILED DESCRIPTION OF THE INVENTION

Figure 1:
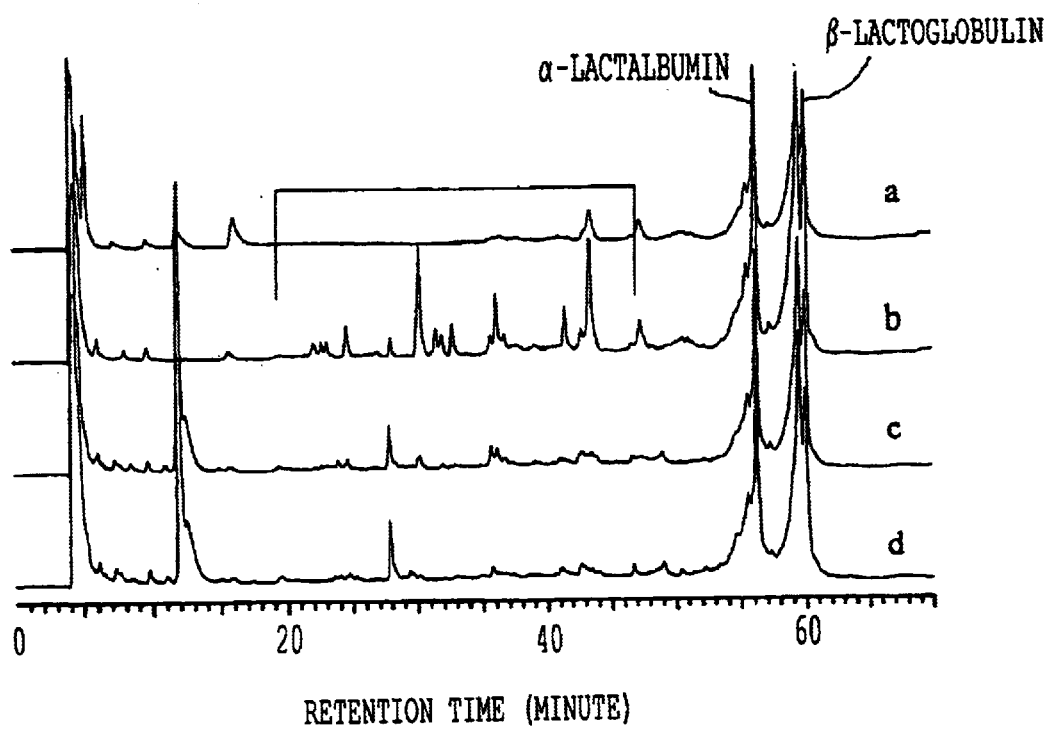
FIG. 1 shows a test result indicating incorporation of a whey protein (partial hydrolysate) in casein (Test Example 1).

The present invention will be described hereinafter in detail.

A cheese manufacturing method with the present invention applied thereto, for enhancing a cheese yield is not particularly limited as long as the cheese manufacturing method includes steps of subjecting a material milk to a milk coagulating treatment and subsequently separating a generated cheese curd and whey. As described above, the material milk can be prepared not only from a whole milk but also from a semi-skim milk, skim milk, and the like. Moreover, for a method of manufacturing a ripened natural cheese, the cheese is manufactured through steps of subjecting the material milk to the coagulating treatment, separating the generated cheese curd from the whey, collecting the separated cheese curd, squeezing the curd, adding salt to the curd, and ripening the curd. However, it goes without saying that a cheese yield enhancing method of the present invention can be applied even to a non-ripened cheese manufacturing method including no ripening step. In the cheese yield enhancing method of the present invention, different from a conventional cheese manufacturing method, the milk coagulating treatment of the material milk to form the cheese curd is performed not by simply allowing a milk coagulating enzyme to act on the material milk (the milk coagulating treatment in a narrow meaning), but by adding/mixing a partial hydrolysate of a whey protein to the material milk beforehand, and applying the milk coagulating enzyme directly to this mixture, or applying TG to the mixture and subsequently applying the milk coagulating enzyme to the mixture (these two types of series of steps can be said to be a milk coagulating treatment in a broad meaning). Thereby, a cheese curd yield, and cheese yield are enhanced. The yield enhancing method has no special relation with a subsequent process of manufacturing the cheese from the cheese curd formed once in this manner.

Additionally, the whey protein has a firm globular structure as it is, that is, in an unmodified state, and does not easily undergo a TG action. In other words, the whey protein cannot form a TG substrate. Therefore, it is a first problem to enhance the action of TG to the whey protein. In order to enhance the action of TG to the whey protein, it is necessary to destroy the globular structure by some treatment. Examples of this method include heating of a disulfide bond present in the whey protein, cutting by chemical or enzymatic reduction, appropriate structure destruction by protease treatment, and the like, and the protease treatment is desirable from viewpoints of application for a food, and convenience. Moreover, among commercial protease such as bromelain, neutrase, papain, and trypsin, from a viewpoint of specificity to the substrate, trypsin is a protease most appropriate for the object of the present invention.

This respect will be described in more detail. TG requires a remaining glutamine group and residual lysine group in reaction of TG. Trypsin has a highest specificity among the aforementioned protease, and cuts a carboxyl terminal end of lysine or arginine (additionally, cutting does not occur between lysine and proline, or between arginine and proline). Therefore, an amino acid of the carboxyl terminal end of the obtained whey protein partial hydrolysate forms lysine or arginine by trypsin treatment, and a possibility of forming the TG substrate is remarkably high. On the other hand, bromelain, neutrase, and papain have a low specificity, low molecular formation excessively advances by the treatment, and these are not suitable for the object of the present invention. Trypsin for use herein is not particularly limited in an origin thereof as long as trypsin has a trypsin activity.

The whey protein to be acted on by protease is not particularly limited, and may be derived from the whey separated by a precedent batch before the cheese manufacturing method of the present invention, or a commercial whey protein (adventitious whey protein) may appropriately be used. A solid content concentration of the partial hydrolysate of the whey protein of the present invention can be used in a range of 0.5 to 20 wt %. For example, an aqueous solution having a concentration of 2 to 20 wt %, preferably 5 to 10 wt % is formed of a commercial powdered whey protein, and an appropriate amount of protease, for example, 1/50 to 1/200 part by weight (protein weight conversion) of trypsin (e.g., specific activity: $2 \times 10^6$ units/g) is added per one part by weight of the whey protein in the aqueous solution. The obtained mixture is retained, for example, at room temperature to 50° C. for four hours to overnight to develop a trypsin enzyme action, and the whey protein is partially hydrolyzed until a hydrolysis degree reaches about 40 to 90%. Subsequently, this is heated, for example, at 80° C. for four minutes, and trypsin is deactivated. The solid content concentration of the partial hydrolysate of the whey protein which can be prepared in this manner is in a range of about 2 to 20 wt %. Additionally, according to the present invention, the partial hydrolysate of the whey protein obtained by performing a protease treatment in this manner is sometimes called a whey protein decomposed material.

The whey protein decomposed material obtained by the protease treatment (e.g., the trypsin treatment) in this manner is subsequently added/mixed to the material milk, and the mixture is subjected directly to the milk coagulating treatment, or acted on by TG and subsequently subjected to the milk coagulating treatment.

Here, TG for use is not particularly limited as long as TG has TG activity, and an origin thereof is not particularly limited. For example, TG derived from microorganisms belonging to Streptoverticillium group, and the like (see Japanese Patent Application Laid-Open No. 27471/1989), derived from mammals such as a guinea pig (see Japanese Patent Publication No. 50382/1989), derived from fishes such as a codfish (Nobuo Seki et al., "Journal of Japan Marine Society", Vol. 56, No. 1, p. 125 (1990)), and obtained by a genetic recombination method utilizing biotechnology (see Japanese Patent Application Laid-Open Nos. 300889/1989, 199883/1993, and 225775/1994), and the like can be used. Among these, TG derived from the microorganism is preferably used because this acts without any calcium and can be obtained in large quantities, and for other reasons.

An added/mixed amount of the whey protein decomposed material to the material milk is determined from a viewpoint of practical use. To the material milk the whey protein decomposed material is added and mixed so that a total weight of the latter (whey protein decomposed material) is in a range of 2 to 20 wt %, preferably 5 to 10 wt % (more stringent) with respect to the total weight of the former (material milk). Additionally, when the whole milk, semi-skim milk, skim milk, and the like are used as the material milk, the solid content concentration of the material milk is usually of the order of 8 to 16 wt %. Therefore, when both components are represented by solid content conversion, the whey protein decomposed material is added/mixed to the material milk at a ratio of one part by weight to 2 to 1,600, preferably 4 to 640 parts by weight.

The obtained mixture may immediately be subjected to the milk coagulating treatment by the milk coagulating enzyme, or acted on by TG and subsequently subjected to the milk coagulating treatment. Preferably, the mixture is allowed to stand at low temperature (e.g., about 5 to 15° C.) overnight for sufficient affinity of the whey protein decomposed material for the material milk. Examples of such operation include an operation of retaining the material milk mixed with the whey protein decomposed material at 5 to 15° C. for 5 to 24 hours, preferably 12 to 16 hours. By the operation, the affinity of the material milk for the whey protein decomposed material is enhanced. In the subsequent milk coagulating treatment, or the milk coagulating treatment after TG treatment, an efficiency of incorporating the whey protein decomposed material in casein can be enhanced.

When the mixture of the material milk and whey protein decomposed material is acted on by TG and subjected to the milk coagulating treatment, TG added amount (used amount) is usually in a range of 0.1 to 50 units, preferably 1 to 10 units per 1 g of a material protein (total protein of the material milk and protein derived from the whey) from a viewpoint of usual enzyme/substrate reaction. Any person skilled in the art can appropriately select enzyme treatment conditions for developing a TG enzyme action in this range, that is, temperature and time of enzyme treatment. The enzyme treatment can usually be performed at room temperature to 40° C. For example, when the enzyme treatment is performed at 31° C., the treatment conditions of two hours for the TG used amount of 3 units per 1 g of protein, and about 30 minutes for the amount of 10 units are sufficient. After TG is activated to such degree, the enzyme action of TG is deactivated. The deactivation is performed by heating TG. For such heating deactivation, for example, after the mixture subjected to the enzyme treatment reaches 80° C., the mixture can be retained for 30 seconds to five minutes, preferably for one minute.

Additionally, the unit of the present invention is a TG activity unit, and measured and defined as follows. That is, in a tris buffer solution at temperature of 37° C. with pH 6.0, TG is activated by a reaction system in which benzyl oxycarbonyl-L-glutamilglycine and hydroxylamine are substrates. A generated hydroxamic acid is formed into an iron complex under existence of trichloroacetic acid. Subsequently, absorbance in 525 nm is measured, and a hydroxamic acid amount is obtained from a working curve. In this case, an enzyme for generating the hydroxamic acid at a ratio of 1 $\mu$mol per one minute is defined as the TG activity unit, that is, one unit (1 U) (see Japanese Patent Application Laid-Open No. 27471/1989).

The mixture of the material milk and whey protein decomposed material is directly subjected to the milk coagulating treatment using the milk coagulating enzyme, or subjected to the TG treatment and subsequently to the milk coagulating treatment. As well known, in addition to the milk coagulating enzyme, a cheese starter, and the like are also usually used in the milk coagulating treatment. That is, the milk coagulating treatment includes "oxidation" in which the cheese starter is added to the mixture of the material milk and whey protein decomposed material subjected to the TG treatment or to no TG treatment, and "coagulation (rennetting)" by action of the milk coagulating enzyme (rennet). There are a large number of types of cheeses, but the present invention is intended for all cheeses in a manufacturing process including a milk coagulating enzyme step by rennet treatment.

Additionally, when the mixture of the material milk and whey protein decomposed material is acted on by TG, TG deactivating treatment is performed, subsequently the mixture is retained at a constant temperature (usually 30 to 35° C.), and the milk coagulating enzyme, and the starter if necessary are added to the mixture. Moreover, if necessary, calcium for accelerating curd formation can also be added. The milk coagulating treatment itself can appropriately be performed in conformity with a known milk coagulating treatment. Furthermore, if necessary, the cheese curd obtained by the milk coagulating treatment is appropriately subjected to usual squeezing, salt addition, ripening treatment, and the like, and the cheese is completed.

As described above, according to the present invention, the affinity of the whey protein for casein in the material milk is increased by partially hydrolyzing the protein. Additionally, the partial hydrolysate of the whey protein is incorporated in casein of the material milk by the TG action through crosslinking reaction, and the cheese curd yield can be enhanced.

EXAMPLES

The present invention will be described hereinafter in more detail by means of a test example and an example.

Test Example 1

Incorporation of Whey Protein Decomposed Material into Casein

The present test example indicates that the whey protein untreated with protease cannot form the TG substrate, and is not incorporated in casein. However, the whey protein partially hydrolyzed by treatment with trypsin (a type of protease) is enhanced in affinity for casein, and additionally incorporated in casein by the TG action through the crosslinking reaction.

A commercial powder whey protein was dissolved in a distilled water to indicate a concentration of 6 wt %. After pH of the solution was neutralized with a dilute hydrochloric acid or dilute sodium hydroxide solution, the solution was retained at constant temperature of 40° C., and trypsin (manufactured by Sigma Co., Ltd., specific activity $2 \times 10^6$ units/g) was added to the solution at a ratio of 1/100 part by weight to the whey protein by means of protein conversion to form an enzyme reactant solution. The solution was retained at the constant temperature for four hours to activate trypsin. After the reaction was finished, the solution was heated at 80° C. for four minutes, trypsin was deactivated, and the solution was then cooled. That is, the whey protein decomposed material was obtained.

Subsequently, the whey protein decomposed material was added/mixed to an aqueous solution of a commercial powder skim milk (obtained by dissolving 10 g of powder milk in a distilled water and setting a total amount to 100 mL) at a volume ratio of 1:9, and a whey protein decomposed material solution having a concentration of 0.6 wt % was prepared. Subsequently, the mixture solution was retained at 4 to 6° C. for 16 hours, and the affinity of a skim milk protein for the whey protein decomposed material was increased. Subsequently, the mixture solution was warmed at 31° C., and TG derived from the microorganism was added to the mixture solution at a ratio of 50 units per 1 g of protein contained in the solution. Immediately after the addition, and about 24 hours after the addition, a part of the solution was extracted, and subjected to rennet treatment (see accompanying FIGS. 1(c) and (d)). A casein curd coagulated by rennet was removed, and a supernatant was subjected to reversed phase high performance liquid chromatography provided with a negative phase column. Moreover, this operation was performed while omitting the TG treatment (see FIG. 1(b)). Furthermore, a control test was performed using no whey protein decomposed material without performing the TG treatment (see FIG. 1(a)).

Results are shown in FIG. 1, in which (a) shows a supernatant of the solution of only a skim milk protein as a control sample subjected to the rennet treatment; (b) shows a supernatant of a mixture solution of the skim milk and whey protein decomposed material subjected to no TG treatment and subjected to the rennet treatment; (c) shows a supernatant of a rennet-treated mixture solution of the skim milk and whey protein decomposed material immediately after adding TG to the solution; and (d) shows a supernatant similar to the supernatant of (c), subjected to the TG treatment for 19.5 hours and subsequently subjected to the rennet treatment. Additionally, when no TG treatment is performed, as shown in (b), the added whey protein decomposed material is detected as a large number of peaks shown in a chromatogram middle portion (between 20 and 50 minutes as a retention time). On the other hand, when the TG treatment is performed ((c) and (d)), the peaks detected in the middle portion are not recognized on the chromatogram with an increase of TG treatment time. Therefore, it is seen that the TG action allows numerous peaks shown in (b) to be incorporated in a casein fraction coagulated by the rennet treatment. That is, it is seen that even when the whey protein decomposed material is used, more whey protein (decomposed material) can be incorporated in the casein fraction with the TG treatment than without the TG treatment.

Figure 2:
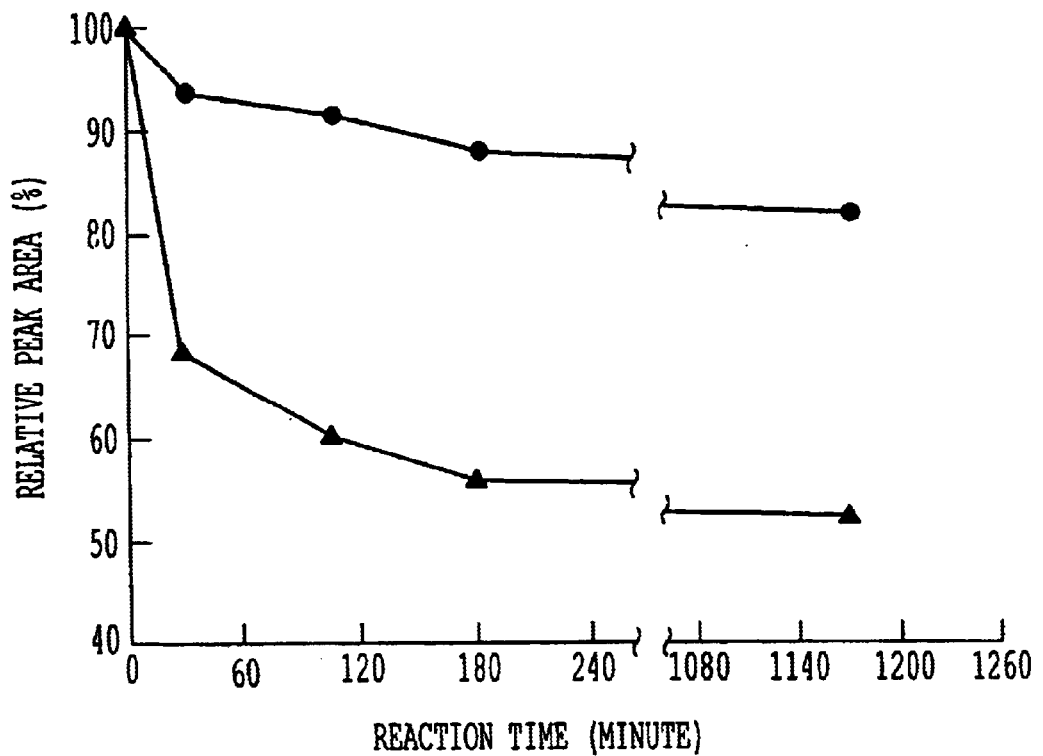
FIG. 2 shows a test result indicating incorporation of the whey protein (partial hydrolysate) in casein by TG (Test Example 2).

FIG. 2 shows a result of measurement of an incorporated amount of whey protein decomposed material with an elapse of time. Conditions are similar to those of FIG. 1, (a) shows a case in which no TG is added (corresponding to FIGS. 1(b)), and (b) shows a case in which the TG is added (corresponding to FIGS. 1(c) and (d)). The amount of the whey protein decomposed material incorporated in the casein fraction is shown with a relative value of a peak area (between 20 and 50 minutes as the retention time) of a whey protein decomposed material portion shown in FIG. 1(a) to a total amount. This result shows that the whey protein decomposed material is incorporated in the casein fraction by about 15% with an increase of reaction time even without adding TG. When TG is added, the peak area largely drops, and the area is about 55% of the total area after 19.5 hours. This indicates that about 45% of whey protein decomposed material is incorporated in the casein fraction.

From these results, it is apparent that the whey protein in an unmodified state (protease untreated) cannot form the TG substrate, and is not incorporated in casein, but the whey protein partially hydrolyzed by the trypsin treatment increases affinity for casein, and is incorporated in casein additionally by the TG action.

Example 1

Cheese Curd Preparation and Yield

Similarly as Test Example 1, the commercial powder whey protein was dissolved in the distilled water to indicate a concentration of 6 wt %. After pH of the solution was neutralized, the solution was retained at constant temperature of 40° C., and the same trypsin as that in Test Example 1 (manufactured by Sigma Co., Ltd.) was added to the solution at a ratio of 1/100 part by weight to the whey protein by means of protein conversion to form the enzyme reactant solution. The solution was retained at the constant temperature for four hours to activate trypsin. After the reaction was finished, the solution was heated at 80° C. for four minutes, trypsin was deactivated, the solution was then cooled, and the whey protein decomposed material was obtained. Subsequently, the whey protein decomposed material was added/mixed to a commercial low-temperature pasteurized milk at a volume ratio of 1:9, and a whey protein decomposed material solution having a concentration of 0.6 wt % was prepared. Additionally, as a control sample, the commercial low-temperature pasteurized milk with no whey protein decomposed material added thereto was used as it is. Both the solutions with TG added and with no TG added were used as test samples, and therefore four types of test solutions were prepared. That is, the following four types were prepared: (a) milk (control sample); (b) milk (with TG added thereto); (c) milk (with no TG added) in which the whey protein decomposed material was added at a ratio of 10% to the milk amount; and (d) milk (with TG added) in which the whey protein decomposed material was added at a ratio of 10% to the milk amount.

Additionally, the TG added amount was set to 3 units per 1 g of total protein derived from the milk and whey protein decomposed material, and time of reaction by TG was set to two hours. After the TG reaction was finished, the reacted mixture was heated at 80° C. for five minutes and TG was deactivated. Each test solution was cooled at 31° C., 30 g of each solution was taken in a test tube, 20 mg of calcium chloride and 15 mg of rennet were added to the solution and the rennet treatment was performed. Subsequently, centrifugal separation of 5,000 g of solution was performed, and a coagulated material obtained by the rennet treatment was recovered as the cheese curd. Moisture was removed from the recovered curd by freeze drying, and a dried material weight was calculated. Moreover, a lactose content in the curd was also measured.

Results are shown in the following table 1. As a result, the control sample (a) had a curd dry weight of 1.0475 g. The value slightly increased to 1.0714 g by adding TG. On the other hand, as shown in (c), when the whey protein decomposed material was added, the value was 1.2554 g without adding TG. When TG was added, the value was 1.4331 g and an obvious increase was recognized. Subsequently, the lactose content in the curd was calculated, the lactose content was subtracted from the curd dried material weight, and a portion derived from the incorporated protein in the increased curd weight was calculated. As a result, in the milk (b) with only TG added thereto, a protein increase ratio was about 5%. In the milk (c) with the whey protein decomposed material added thereto, the increase ratio was 23%. In the milk (d) with the whey protein and TG added thereto, the increase ratio was 27% and the ratio of the protein in the curd increased. These indicate that the cheese curd yield can remarkably be enhanced by adding/mixing the whey protein decomposed material to the material milk and allowing TG to act on the mixture during manufacturing of the cheese.

TABLE 1

Cheese curd yield

| Test solution: milk (whey decomposed material/TG) | Curd dry material weight (g) | Lactose in dry curd (g) | Protein increase amount (g) |
|---|---|---|---|
| (a) Milk (non-/non-added) | 1.0475 | 0.318 | 0 (0%) |
| (b) Milk (non-added/added) | 1.0714 | 0.306 | +0.036 (5%) |
| (c) Milk (added/non-added) | 1.2554 | 0.360 | +0.166 (23%) |
| (d) Milk (added/added) | 1.4331 | 0.506 | +0.198 (27%) |

[Effects of the Invention]

According to the present invention, when a whey protein is treated protease such as trypsin, and a whey protein partial hydrolysate is formed, reactivity with TG can be enhanced, which has heretofore been difficult. Moreover, when the hydrolysate is mixed with a material milk, and the mixture is directly subjected to milk coagulating treatment, or the mixture is acted on by TG and subsequently subjected to the milk coagulating treatment, incorporation of the whey protein (partial hydrolysate) in casein can remarkably be enhanced. Therefore, according to the present invention, more cheese can be manufactured from a constant amount of material milk.

What is claimed is:

1. A method for producing cheese, comprising:
    (1) mixing a partial hydrolysate of milk whey protein with a milk material, to obtain a first mixture;
    (2) coagulating said mixture with a milk coagulating enzyme, to obtain a second mixture comprising cheese curd and whey,
    wherein said mixing said partial hydrolysate of milk whey protein with said milk material is carried out by:
        (a) adding said partial hydrolysate of milk whey protein to said milk material, to obtain an initial mixture;
        (b) maintaining said initial mixture at a temperature of 2 to 15° C. for 5 to 24 hours, to obtain an incubated mixture; and
        (c) treating said incubated mixture with transglutaminase.

2. The method of claim 1, further comprising:
    (3) separating said cheese curd from said whey.

3. The method of claim 1, wherein said partial hydrolysate of milk whey protein is prepared by treating milk whey protein with a protein decomposing enzyme.

4. The method of claim 3, wherein said protein decomposing enzyme is selected from the group consisting of bromelain, neutrase, papain, and trypsin.

5. The method of claim 3, wherein said protein decomposing enzyme is trypsin.

6. The method of claim 1, wherein said partial hydrolysate of milk whey protein is mixed with said milk material in an amount of 2 to 20 wt % of said partial hydrolysate of milk whey protein, based on the total weight of said milk material.

7. The method of claim 1, wherein said partial hydrolysate of milk whey protein is mixed with said milk material in an amount of 5 to 10 wt % of said partial hydrolysate of milk whey protein, based on the total weight of said milk material.

8. The method of claim 1, wherein said partial hydrolysate of milk whey protein and said milk material are mixed in relative amounts of 2 to 1,600 parts by weight of said milk material and one part by weight of said partial hydrolysate of milk whey protein, based on the solid contents of said milk material and said partial hydrolysate of milk whey protein.

9. The method of claim 1, wherein said partial hydrolysate of milk whey protein and said milk material are mixed in relative amounts of 4 to 640 parts by weight of the said milk material and one part by weight of said partial hydrolysate of milk whey protein, based on the solid contents of said milk material and said partial hydrolysate of milk whey protein.

10. The method of claim 1, wherein said initial mixture is maintained at a temperature of 2 to 15° C. for 12 to 16 hours.

11. The method of claim 1, wherein said milk material is selected from the group consisting of whole milk, semi-skim milk, and skim milk.

12. A method for producing cheese, comprising:
    (1) mixing a partial hydrolysate of milk whey protein with a milk material, to obtain a first mixture;
    (2) treating said first mixture with transglutaminase, to obtain a second mixture; and
    (3) coagulating said second mixture with a milk coagulating enzyme, to obtain a mixture comprising cheese curd and whey.

13. The method of claim 12, further comprising:
    (4) separating said cheese curd from said whey.

14. The method of claim 12, wherein said partial hydrolysate of milk whey protein is prepared by treating milk whey protein with a protein decomposing enzyme.

15. The method of claim 14, wherein said protein decomposing enzyme is selected from the group consisting of bromelain, neutrase, papain, and trypsin.

16. The method of claim 14, wherein said protein decomposing enzyme is trypsin.

17. The method of claim 12, wherein said partial hydrolysate of milk whey protein is mixed with said milk material in an amount of 2 to 20 wt % of said partial hydrolysate of milk whey protein, based on the total weight of said milk material.

18. The method of claim 12, wherein said partial hydrolysate of milk whey protein is mixed with said milk material in an amount of 5 to 10 wt % of said partial hydrolysate of milk whey protein, based on the total weight of said milk material.

19. The method of claim 12, wherein said partial hydrolysate of milk whey protein and said milk material are mixed in relative amounts of 2 to 1,600 parts by weight of said milk material and one part by weight of said partial hydrolysate of milk whey protein, based on the solid contents of said milk material and said partial hydrolysate of milk whey protein.

20. The method of claim 12, wherein said partial hydrolysate of milk whey protein and said milk material are mixed in relative amounts of 2 to 1,600 parts by weight of said milk material and one part by weight of said partial hydrolysate of milk whey protein, based on the solid contents of said milk material and said partial hydrolysate of milk whey protein.

21. The method of claim 12, wherein said partial hydrolysate of milk whey protein and said milk material are mixed in relative amounts of 4 to 640 parts by weight of the said milk material and one part by weight of said partial hydrolysate of milk whey protein, based on the solid contents of said milk material and said partial hydrolysate of milk whey protein.

22. The method of claim 12, wherein said milk material is selected from the group consisting of whole milk, semi-skim milk, and skim milk.

* * * * *